US010478525B2

(12) United States Patent
Shelby et al.

(10) Patent No.: US 10,478,525 B2
(45) Date of Patent: *Nov. 19, 2019

(54) PROCESS FOR DEMINERALIZATION OF BONE MATRIX WITH PRESERVATION OF NATURAL GROWTH FACTORS

(71) Applicant: Bacterin International, Inc., Belgrade, MT (US)

(72) Inventors: Nancy J. Shelby, Anchorage, AK (US); Steven M. Scott, Salt Lake City, UT (US); Benjamin P. Luchsinger, Bozeman, MT (US); Gregory A. Juda, Bozeman, MT (US); Kelly R. Kirker, Bozeman, MT (US); Darrel L. Holmes, Bozeman, MT (US); Jesus Hernandez, Universal City, TX (US)

(73) Assignee: BACTERIN INTERNATIONAL, INC., Belgrade, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/812,777

(22) Filed: Jul. 29, 2015

(65) Prior Publication Data

US 2015/0328366 A1    Nov. 19, 2015

Related U.S. Application Data

(60) Continuation of application No. 14/186,993, filed on Feb. 21, 2014, now Pat. No. 9,114,191, which is a continuation of application No. 13/453,818, filed on Apr. 23, 2012, now Pat. No. 8,992,964, which is a division of application No. 12/130,384, filed on May 30, 2008, now Pat. No. 8,574,825.

(60) Provisional application No. 60/932,848, filed on Jun. 1, 2007.

(51) Int. Cl.
| A61L 27/36 | (2006.01) |
| C12N 5/00 | (2006.01) |
| A61F 2/46 | (2006.01) |
| A61L 27/38 | (2006.01) |
| A61L 27/54 | (2006.01) |
| A61L 27/56 | (2006.01) |
| A61L 27/22 | (2006.01) |
| A61L 27/28 | (2006.01) |

(52) U.S. Cl.
CPC ........ A61L 27/3608 (2013.01); A61F 2/4644 (2013.01); A61L 27/227 (2013.01); A61L 27/28 (2013.01); A61L 27/3683 (2013.01); A61L 27/3691 (2013.01); A61L 27/38 (2013.01); A61L 27/3804 (2013.01); A61L 27/3834 (2013.01); A61L 27/54 (2013.01); A61L 27/56 (2013.01); C12N 5/0062 (2013.01); C12N 5/0068 (2013.01); A61L 2300/414 (2013.01); A61L 2420/00 (2013.01); A61L 2430/02 (2013.01); A61L 2430/06 (2013.01); C12N 2503/02 (2013.01); C12N 2533/90 (2013.01); C12N 2537/00 (2013.01)

(58) Field of Classification Search
None
See application file for complete search history.

(56) References Cited

U.S. PATENT DOCUMENTS

| 5,507,813 A | 4/1996 | Dowd et al. |
| 5,531,791 A | 7/1996 | Wolfinbarger, Jr. |
| 5,541,107 A | 7/1996 | Naughton et al. |
| 6,855,169 B2 | 2/2005 | Boyer, III et al. |
| 6,863,900 B2 | 3/2005 | Kadiyala et al. |
| 6,998,135 B1 | 2/2006 | Sunwoo et al. |
| 7,172,629 B2 | 2/2007 | McKay |
| 7,323,193 B2 | 1/2008 | Morris et al. |
| 7,582,309 B2 | 9/2009 | Rosenberg et al. |
| 7,744,597 B2 | 6/2010 | Gaskins et al. |
| 7,939,108 B2 | 5/2011 | Morris et al. |
| 8,529,962 B2 | 9/2013 | Morris et al. |
| 2003/0143258 A1 | 7/2003 | Knaack et al. |
| 2004/0101959 A1* | 5/2004 | Marko ................ A61L 27/3839 435/366 |
| 2005/0244450 A1 | 11/2005 | Reddi et al. |
| 2005/0281856 A1 | 12/2005 | McGlohorn et al. |
| 2006/0134781 A1* | 6/2006 | Yang ..................... C12N 5/0667 435/366 |
| 2006/0210644 A1 | 9/2006 | Levin |
| 2006/0216323 A1 | 9/2006 | Knaack et al. |
| 2008/0033572 A1 | 2/2008 | D'Antonio et al. |

FOREIGN PATENT DOCUMENTS

WO    WO 2006/076659    7/2006

OTHER PUBLICATIONS

Mathiowetz et al., Grip and Pinch Strength: Normative Data for Adults, Arch Phys Med Rehabil, vol. 66, pp. 69-72, 1985.*
Pietrzak et al., BMP depletion occurs during prolonged acid demineralization of bone: characterization and implications for graft preparation, Cell Tissue Bank (2011) vol. 12, pp. 81-88.*
Sherman et al., PORON Cushioning Blog, 2016, retrieved from the internet: http://blog.poroncushioning.com/the-rule-of-thumb-for-measuring-foam-cushioning-properties-in-footwear/.*
Blum et al. "Measurement of Bone Morphogenetic Proteins and Other Growth Factors in Demineralized Bone Matrix," Orthopedics, Jan. 2004, vol. 27, No. 1, supplement, pp. s161-s165.

(Continued)

Primary Examiner — Thomas J. Visone
Assistant Examiner — Evelyn Y Pyla
(74) Attorney, Agent, or Firm — Sheridan Ross PC

(57) ABSTRACT

A demineralized bone matrix is produced by a process in which a bone body is placed in a first processing solution comprising an acid to demineralize the bone body. The bone body is periodically removed from the first solution at specific time intervals to perform at least one test, such as a compression test, on a mechanical property of the bone body. When the test yields a desired result, the bone body is exposed to a second processing solution that is less acidic than the first, thus minimizing the exposure of the bone body to the harsh acidic conditions of the demineralization phase of the process.

20 Claims, 5 Drawing Sheets

(56) References Cited

OTHER PUBLICATIONS

Official Action for U.S. Appl. No. 14/672,608, dated Jul. 18, 2016 13 pages.
Official Action for U.S. Appl. No. 14/672,727, dated Aug. 2, 2016 17 pages.
Official Action for U.S. Appl. No. 14/672,763, dated Aug. 3, 2016 18 pages.
U.S. Tissue and Cell Standard Operating Policy and Procedure dated Mar. 28, 2005. (Exhibit 1).
Bacterin MS Processing—Demineralization of OsteoSponge, OsteoFiller and OsteoWrap (Document No. SOP 210-8007-0) dated Aug. 22, 2007. (Exhibit 2).
Bacterin MS Processing—Demineralization of OsteoSponge, OsteoFiller and OsteoWrap (Document No. SOP 210-8007-1) (showing track changes) not dated. (Exhibit 3).
Bacterin MS Processing—Demineralization of OsteoSponge, OsteoFiller and OsteoWrap (Document No. SOP 210-8007-1) dated Oct. 1, 2007. (Exhibit 4).
"Cementing Knowledge: MTS helps a leading Swedish research tema pursue the next generation of spinal bone cements." MTS Systems Corporation, 2011, 2 pages.
"OsteoSponge™—Marketing Brochure 5041A," Bacterin International, Inc., Mar. 2006, 4 pages.
"Standards for Tissue Banking," American Association of Tissue Banks, 11th Ed., Jan. 1, 2007, excerpts from Introduction and Section E "Processing, Preservation, quarantine, and Storage," 20 pages.
Finkemeier "Bone-Grafting and Bone-Graft Substitutes," The Journal of Bone and Joint Surgery, 2002, vol. 84, pp. 454-464.
Pietrzak et al., "Assay of Bone Morphogenetic Protein-2, -4 and -7 in Human Demineralized Bone Matrix," Journal of Craniofacial Surgery, Jan. 2006, vol. 17, No. 1, pp. 84-90.
Pietrzak, "Musculoskeletal Tissue Regeneration: Biological Materials and Methods (Google eBook)," Fig. 6.7, 2008, available at www.books.google.com/books/about/Musculoskeletal_Tissue_Regeneration.html?id=2qq56LYomagC, 2 pages.
Radwin et al., "External finger forces in submaximal five-finger static pinch prehension," Ergonomics, 1992, vol. 35, Iss. 3, pp. 275-288.
Swartz "Decalcified and Undecalcified Vancellous Bone Block Implants Do Not Heal Diaphyseal Defects in Dogs," Orthopaedic and Trauma Surgery, 1991, vol. 111, No. 1, pp. 47-50.
Turonis et al., "The Effect of Residual Calcium in Decalcified Freeze-dried Bone Allograft in a Critical-sized Defect in the Rattus norvegicus Cavarium," Journal of Oral Implantology, 2006, vol. 32, No. 2, pp. 55-62.
International Search Report for International (PCT) Patent Application No. PCT/US08/06942, dated Oct. 9, 2008, 4 pages.
Written Opinion for International (PCT) Patent Application No. PCT/US08/06942, dated Oct. 9, 2008, 4 pages.
Official Action for Canadian Patent Application No. 2,695,492, dated Jul. 24, 2014, 4 pages.
Extended European Search Report for European Patent Application No. 08768038.5 dated Oct. 5, 2012, 9 pages.
Official Action for European Patent Application No. No. 08768038.5 dated Jul. 25, 2013, 5 pages.
Notice of Intention to Grant for European Patent Application No. No. 08768038.5 dated Apr. 11, 2014, 5 pages.
Official Action (English translation) for Korean Patent Application No. 10-2009-7027606, dated Jun. 23, 2014, 6 pages.
Official Action for U.S. Appl. No. 12/130,384, dated Sep. 21, 2011 12 pages.
Official Action for U.S. Appl. No. 12/130,384, dated May 31, 2012 16 pages.
Official Action for U.S. Appl. No. 12/130,384, dated Feb. 26, 2013, 18 pages.
Notice of Allowance for U.S. Appl. No. 12/130,384, dated Sep. 13, 2013, 10 pages.
Official Action for U.S. Appl. No. 13/453,818, dated Aug. 6, 2012 6 pages.
Official Action for U.S. Appl. No. 13/453,818, dated Jan. 4, 2013, 8 pages.
Official Action for U.S. Appl. No. 13/453,818, dated Oct. 16, 2013, 13 pages.
Official Action for U.S. Appl. No. 13/453,818, dated Apr. 25, 2014, 16 pages.
Notice of Allowance for U.S. Appl. No. 13/453,818, dated Nov. 21, 2014, 7 pages.
Notice of Allowance for U.S. Appl. No. 13/453,818, dated Mar. 31, 2015, 12 pages.
Final Action for U.S. Appl. No. 14/672,727, dated Feb. 9, 2017 23 pages.
Final Action for U.S. Appl. No. 14/672,763, dated Feb. 27, 2017 23 pages.
Official Action for U.S. Appl. No. 14/812,777, dated Mar. 1, 2017 22 pages.
Chakkalakal et al. "Demineralized Bone Matrix as a Biological Scaffold for Bone Repair," Tissue Engineering, 2001, vol. 7, No. 2, pp. 161-177.
Official Action for U.S. Appl. No. 14/672,608, dated Jan. 17, 2018 21 pages.
Official Action for U.S. Appl. No. 14/672,727, dated Jan. 19, 2018 26 pages.
Official Action for U.S. Appl. No. 14/672,763, dated Jan. 19, 2018 19 pages.
Honsawek et al., "Extractable bone morphogenetic protein and correlation with induced new bone formation in an in vivo assay in the athymic mouse model," Cell and Tissue Banking, vol. 6, 2005, pp. 13-23.
Liberman et al., "The Role of Growth Factors in the Repair of Bone," Journal of Bone and Joint Surgery Current Concepts Review, vol. 84A, No. 6, Jun. 2002, pp. 1032-1044.
Tuong et al., "Insulinlike Growth Factor 1- and 2-Augmented Collagen Gel Repair of Facial Osseous Defects," Archives of Otolaryngology—Head & Neck Surgery, vol. 125, No. 4, 1999, pp. 451-455.
Official Action for U.S. Appl. No. 14/672,608, dated Sep. 26, 2018 19 pages.
Official Action for U.S. Appl. No. 14/672,727, dated Sep. 26, 2018 16 pages.
Official Action for U.S. Appl. No. 14/672,763, dated Sep. 26, 2018 16 pages.
Official Action for U.S. Appl. No. 14/672,608, dated Jul. 22, 2019, 26 pages.
Official Action for U.S. Appl. No. 14/672,727, dated Jul. 5, 2019, 26 pages.
Official Action for U.S. Appl. No. 14/672,763, dated Jun. 28, 2019 25 pages.

* cited by examiner

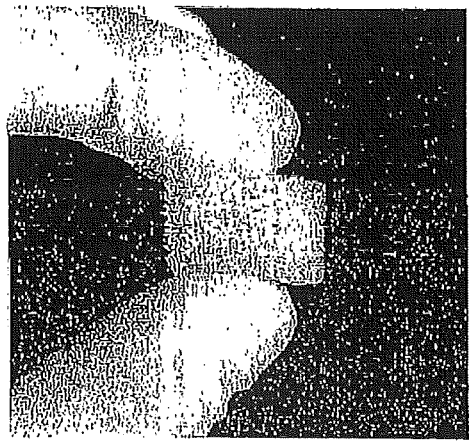
Non-compressed demineralized
cancellous bone block
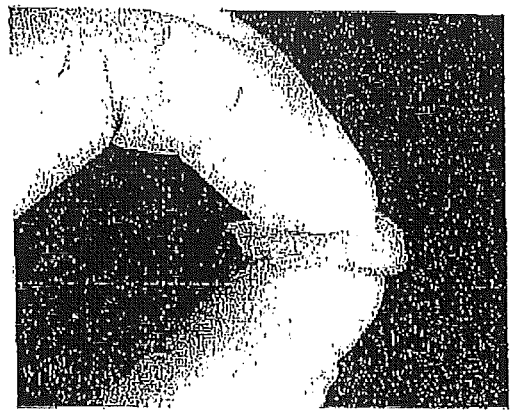
Compressed demineralized cancellous bone
(Assumes original shape without pressure)
FIG. 1A
FIG. 1B Figure 2. IGF-1 content of demineralized cancellous bone matrix under different conditions of acid demineralization.

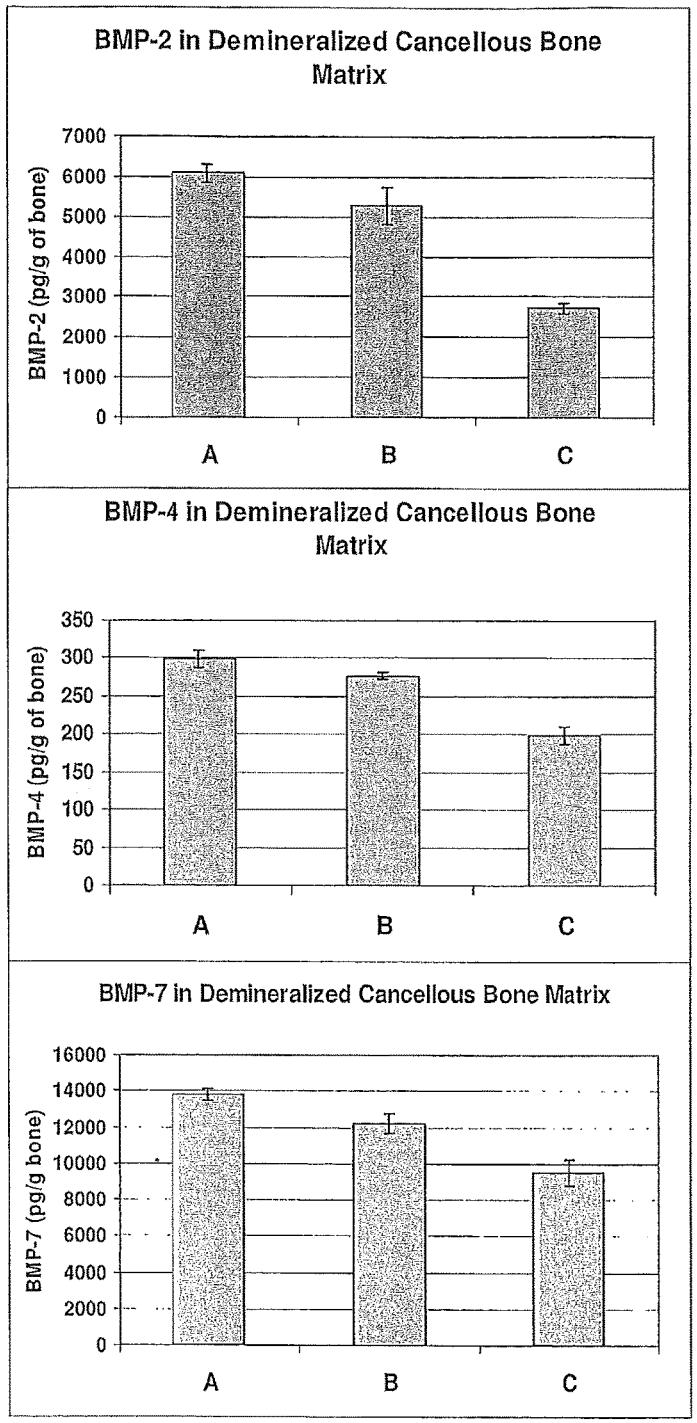
Figures 3a-3c. Growth factor content of demineralized cancellous bone matrix under different conditions of acid demineralization.

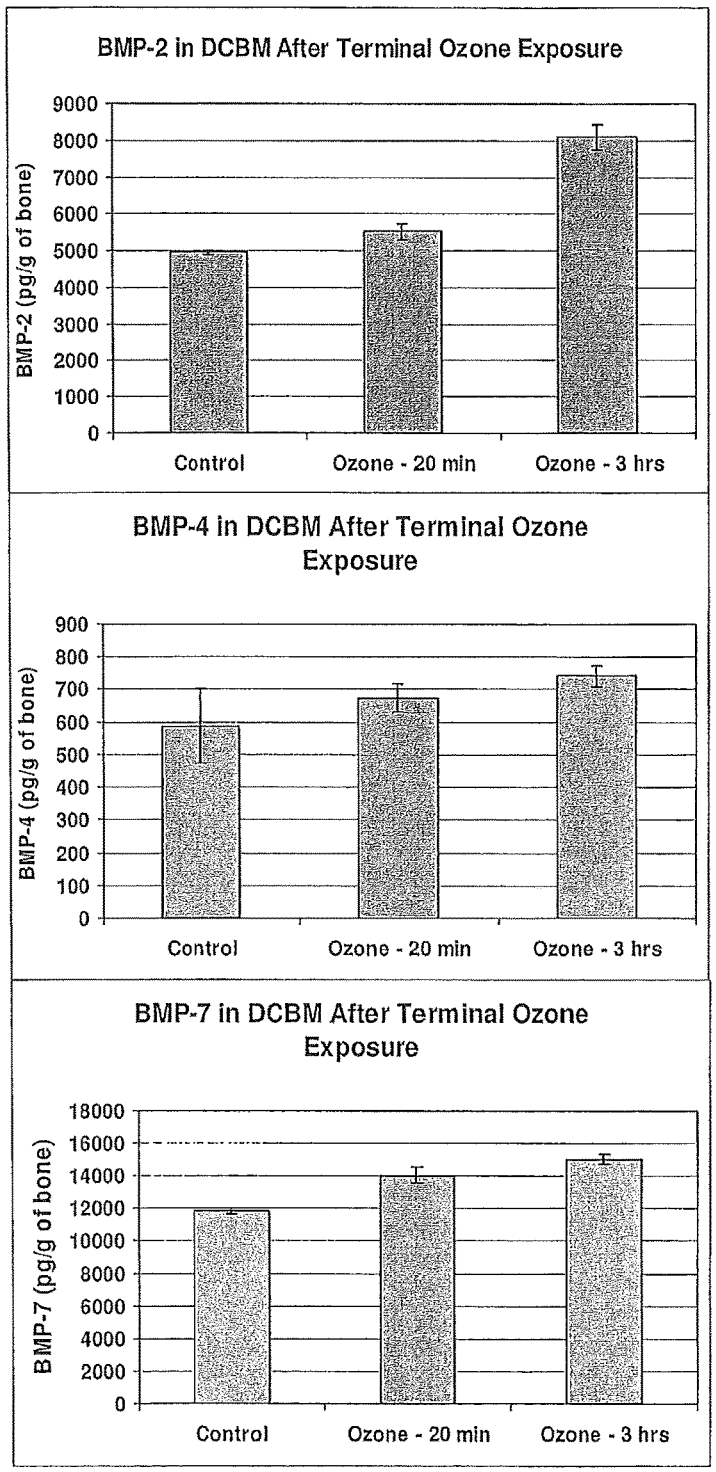
Figures 4a-4c. Growth factor content of demineralized cancellous bone matrix (DCBM) as a function of terminal exposure to ozonated solution.

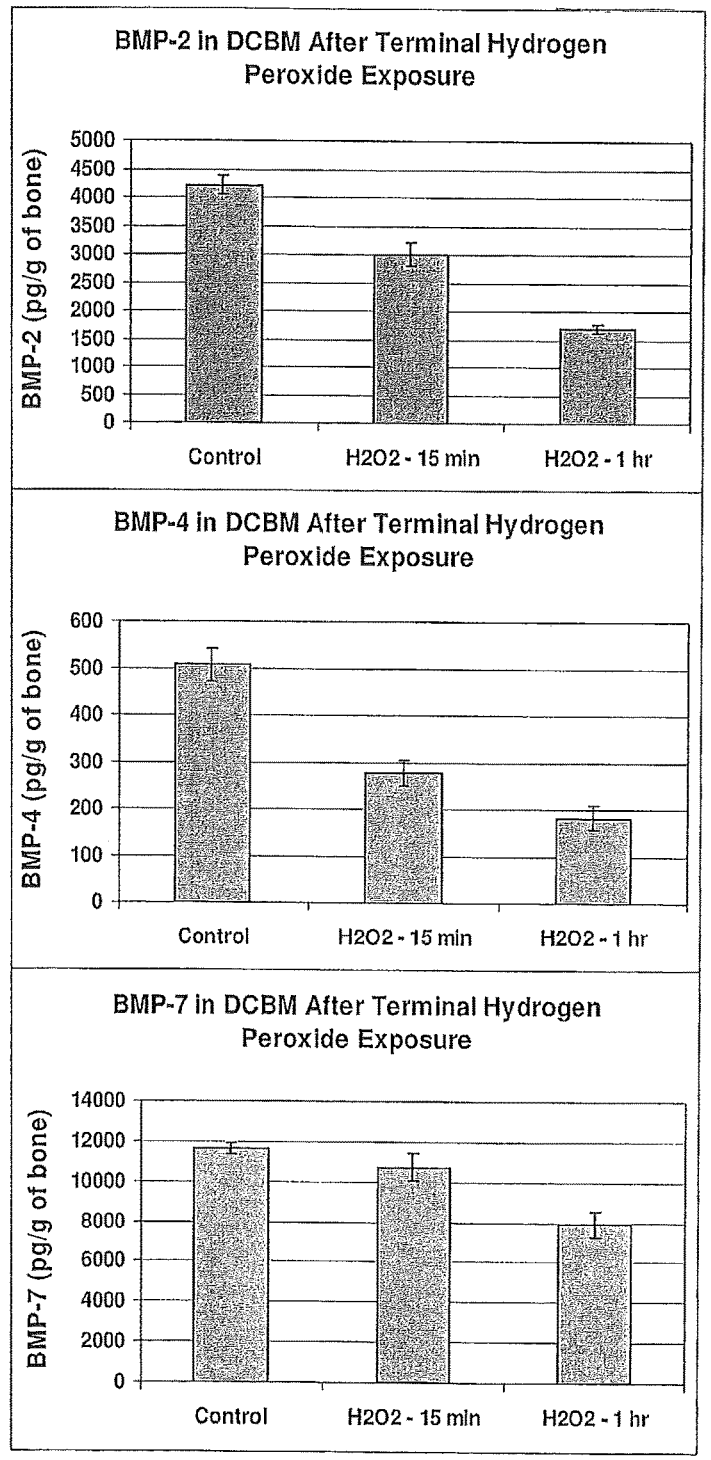
Figures 5a-5c. Growth factor content of demineralized cancellous bone matrix (DCBM) as a function of terminal exposure to hydrogen peroxide solution.

PROCESS FOR DEMINERALIZATION OF BONE MATRIX WITH PRESERVATION OF NATURAL GROWTH FACTORS

CROSS-REFERENCE TO RELATED APPLICATION(S)

This application is a continuation of application Ser. No. 14/186,993, filed on Feb. 21, 2014, which is a continuation of application Ser. No. 13/453,818, filed on Apr. 23, 2012, which issued as U.S. Pat. No. 8,992,964 on Mar. 31, 2015, which is a divisional application of application Ser. No. 12/130,384, filed May 30, 2008, which has issued as U.S. Pat. No. 8,574,825 on Nov. 5, 2013, and claims benefit from Application Ser. No. 60/932,848, entitled PROCESS FOR DEMINERALIZATION OF BONE MATRIX WITH PRESERVATION OF NATURAL GROWTH FACTORS, filed Jun. 1, 2007. This application is also related to application Ser. No. 14/672,608, filed on Mar. 30, 2015, which is a divisional of application Ser. No. 13/453,818, filed on Apr. 23, 2012, which issued as U.S. Pat. No. 8,992,964 on Mar. 31, 2015, which is a divisional application of application Ser. No. 12/130,384, filed May 30, 2008, which has issued as U.S. Pat. No. 8,574,825 on Nov. 5, 2013, and claims benefit from Application Ser. No. 60/932,848. This application is also related to application Ser. No. 14/672,727, filed Mar. 30, 2015, which is a divisional of application Ser. No. 13/453,818, filed on Apr. 23, 2012, which issued as U.S. Pat. No. 8,992,964 on Mar. 31, 2015, which is a divisional application of application Ser. No. 12/130,384, filed May 30, 2008, which has issued as U.S. Pat. No. 8,574,825 on Nov. 5, 2013, and claims benefit from Application Ser. No. 60/932,848. This application is also related to application Ser. No. 14/672,763, filed Mar. 30, 2015, which is a divisional of application Ser. No. 13/453,818, filed on Apr. 23, 2012, which issued as U.S. Pat. No. 8,992,964 on Mar. 31, 2015, which is a divisional application of application Ser. No. 12/130,384, filed May 30, 2008, which has issued as U.S. Pat. No. 8,574,825 on Nov. 5, 2013, and claims benefit from Application Ser. No. 60/932,848. Each reference is incorporated by reference in its entirety.

BACKGROUND

The present invention relates to a process for manufacturing demineralized bone matrix. More specifically, the present invention relates to a method for manufacturing demineralized bone matrix, which focuses on the preservation of native/intrinsic growth factors residing within the matrix while providing unique handling characteristics. The demineralized bone matrix will be used in promoting bone and cartilage repair and bone and cartilage growth and regeneration.

Approximately one million bone graft procedures are conducted each year throughout the world. About 500,000 of these procedures are conducted in the United States, and roughly 250,000 of the bone grafting procedures in the United States involve the spine. These bone graft and bone substitute products may include, for example, bone substitutes, bone dowels, demineralized bone matrix products, including putties, "platelet" helpers, and other allograft bone materials.

Injury to the cartilage of the knee joint is also a common orthopedic problem, affecting millions of people in the United States. Damaged articular cartilage does not normally regenerate itself. Current treatment for cartilage damage requires patients to undergo arthroscopic surgery to relieve their symptoms. If the cartilage cannot be repaired, and must be removed, the patient is likely to develop osteoarthritis, with possible need for further surgeries, including total knee replacement in severe cases.

The use of bone materials to promote bone healing after fracture, bone loss, infection, tumor, or other pathologic conditions is well known to those skilled in the art. Typically, bone grafting employs one of three modalities to promote bone healing. First, an autologous bone graft may be used. An autologous bone graft is derived from the recipient and is commonly taken from the iliac bone. Second, a bone allograft may be used which refers to a graft derived from a separate donor, usually within the same species. Finally, a bone graft substitute may be used that is naturally derived (e.g., from bone chips, granulated bone powder, and the like) or, in the alternative, synthetic or semi-synthetic products, generally in the form of putty and gel type of defect fillers, made up of allogeneic bone chips, granules, or bone powder, with or without carriers.

Autologous bone graft, sometimes referred to as an autograft (i.e., the patient's own bone), may be harvested to supply the needed bone to repair the defect. As appreciated by those skilled in the art, there are many advantages for using autologous bone in bone defect repair. For example, autologous bone is typically viscoelastic, osteoconductive, osteoinductive, and osteogenic (i.e., contains cells in its matrix that promote bone formation). In addition, an autologous bone graft avoids histocompatibility and infectious disease issues. Autologous bone, however, is limited in supply, is generally painful to the patient upon harvesting, and may lead to significant donor site morbidity (i.e., may require additional surgical incisions in the patient, may lead to surgical complications, blood loss and may cause additional patient discomfort, and may ultimately increase patient recovery time).

Allograft bone grafts are advantageous from the standpoint of being available in larger quantities compared to autologous bone grafts. However, allograft bone grafts may present disadvantages relating to histocompatibility issues (e.g., rejection by recipient immune system), the potential harboring of infectious agents, and may also include bone with poor malleable or mechanical characteristics (e.g., elasticity, compressibility, resiliency, and the like) due to high calcium and mineral content. Presently available bone graft substitutes developed by those skilled in the art usually have many of the same disadvantages as outlined above with regards to allograft bone grafts. Bone allograft or synthetic graft substitute products are generally formulated as putty and gel type fillers, designed to be inserted into dead space(s) between bone defects (i.e., defect or void fillers). Traditionally, bone graft substitutes may be made from allogeneic bone chips, granules, or bone powder, or synthetic materials with or without carrier compositions. Additionally, there are a few xenogeneic bone graft products available that are made from bovine bone, and the present invention may be adapted to use other sources of starting material, such as bovine material. Disadvantages are similar to that presented with allografts, including potential immune reaction to xenogeneic bone and infectious agents, including prions.

Another significant disadvantage of the currently available autograft, allograft, and bone substitute products of the prior art is that they are generally unable to resist loading forces and maintain their shape and structural integrity during surgical use for bone repair. To date, no solid, pre-shaped, flexible, elastic product (bone-derived or synthetic) that is able to resist loading forces, deform and then regain its shape and structural integrity is available for surgical use. These characteristics are essential for producing bone repair that closely mimics the normal bone condition in the absence of the bone defect.

In addition, bone graft materials and bone graft substitutes are known to have structural, mechanical and biological characteristics (e.g., lack of compressibility, lack of elasticity, and the like), which hinder their surgical placement, require relatively invasive surgical procedures, or sub-optimally promote bone growth.

Some bone allograft materials or synthetic composites, including ceramics and allograft bone material, have attempted to mimic certain autograft characteristics. For example, prior art ceramic bone graft substitutes, such as tri-calcium phosphate compounds, have osteoconductive activity (i.e., facilitates formation of bone trellis structure by promoting vascularization), but do not have osteoinductive activity (i.e., possess bone morphogenetic proteins that facilitate formation of bone by active recruitment of stem cells from surrounding tissue). Moreover, it has been found that ceramic bone graft substitutes of the prior art may be brittle or fail under forces of compression, torsion, bending, and/or tension.

Prior art bone graft substitutes, including demineralized cortical bone powder and recombinant human bone morphogenic protein (rhBMP), are typically osteoinductive. These bone graft substitutes, however, lack osteoconductive properties and generally have no macrostructure to encourage cell ingrowth and sufficiently resist the forces of compression, torsion, bending, and/or tension. Although larger sized traditional allograft bone products are osteoconductive and have some of the mechanical strength properties of bone, they are less osteoinductive due to their mineral content, cortical structure, and overall density. To date, no grafting material exists that can be deformed, for example compressed, torqued, and/or bent, which possess the mechanical properties to allow it to regain its original shape, structure, and size.

Demineralized cortical bone matrix (DBM) putties developed by those skilled in the art commonly include very small (e.g., micron-sized) particles of cortical allograft bone (e.g., demineralized, nondemineralized, or both) mixed with a carrier to produce a workable putty or gel in varying viscosities. Prior art bone substitute compounds (e.g., putties, gels, solutions, and the like) may be introduced into a bone defect with a spatula, syringe or by hand. Since these prior art bone substitute compounds are malleable, they generally deform to fit irregular spaces. However, since the active particles are typically micron-sized, bone substitute putties, gels, solutions, and the like may not resemble normal bone macroscopically and, in addition, may not contain normal pores, surfaces, spaces, and bone architecture. Moreover, the carriers used in prior art bone substitute compounds generally hold the micron-sized particles in suspension or in a colloid that tends to degrade with time, leaving the construct without normal bony macro-structure. For example, under in vivo conditions and in the presence of saline, blood, and/or blood serum, and during irrigation, many of these bone substitute compounds (e.g., putties, gels, solutions, and the like) break down, dissolve, or ooze out of the bone void at the time of surgery or within minutes or hours after their introduction into the bone defect. Even those prior art bone substitute compounds that do not dissolve in vivo do not resemble normal bone in macrostructure.

In addition, the bone substitute compounds of the prior art may not maintain the general mechanical properties (e.g., elasticity, flexibility, resistance to compression, tension, torsion, bending, or the like) normally attributed to bone. To this end, there are no bone substitute compounds available that can be compressed into a bone void or into a metallic, plastic, or composite implanted matrix with the ability to expand to fit that void and in the process of expansion regain its respective micro and macro shape and size through maintenance of its physical properties or memory.

Studies of demineralized bone products have shown a great variability in osteoinductive potential as measured by various bioassays, including the ALP assay, native/intrinsic BMP levels evaluated by extraction and ELISA assay, and in vivo measures of bone fusion. Factors contributing to this variability may include differences in processing techniques. Varied current practices of delipidification, demineralization and terminal sterilization of bone have the potential to significantly and negatively affect native growth factors contained within the bone matrix. Chemical processing of bone matrix with prolonged exposure to high concentrations of acid or high levels of gamma irradiation all reduce osteoinductive activity of the treated bone. Current practices include demineralization processes that monitor solution pH changes during acid exposure and utilize set concentrations and exposure times to acid. None of the current practices are optimized to preserve native growth factors associated with the bone matrix by reducing exposure to acid. In addition, there is structural variability within cancellous bone found at different sites within the body and between donors (i.e. variation in porosity and density). Such variations significantly affect delipidification and demineralization processing outcomes, even between cancellous bone blocks of the same size. Currently, most experts in the art believe cancellous bone to be only osteoconductive and not osteoinductive (Schwarz 1991, *Arch Orthop Trauma Surg.*) (Finkemeier 2002, *J. Bone Joint Surg.*). This perception is maintained by processing methods that remove, or render inactive, osteoinductive growth factors. The present invention produces a cancellous bone matrix with higher quantities of active growth factors than current art processes. One skilled in the art would recognize that a process that minimizes exposure of the bone matrix to potential damaging agents during processing, optimized to preserve native growth factor levels, would be a considerable advance in the field.

Ozone is a gas with known lethal effects on microorganisms and resultant sterilizing properties that are used extensively in the water and food industries. Ozone is a strong bactericide needing only a few micrograms per milliliter for kill of organisms including aerobic and anaerobic bacteria such as: *Bacteroides, Campylobacter, Clostridium, Corynebacteria, Escherichia, Klebsiella, Legionella, Mycobacteria, Propriobacteria, Pseudomonas, Salmonella, Shigella, Staphylococcus, Streptococcus, Yersinia*, and *Mycobacteria*. It is also effective against viruses, including Flaviviridae, Filoviridae, Hepnaviridae, Herpesviridae, Orthomyxoviridae, Retroviridae. Coronaviridae, Togaviridae, Rhabdoviridae, Bunyaviridae, Pramyxoviridae, and Poxviridae. Non-enveloped susceptible viral families include: Adenoviridae, Picornaviridae, Papillomaviridae, Caliciviridae, Astroviridae, and Reoviridae. Ozone neutralizes microorganisms via a spectrum of mechanisms. Most-studied is ozone oxidation of bacterial lipids and proteins found in bacterial cell membranes, and viral envelope lipids, phospholipids, cholesterols, and glycoproteins. Ozone is also toxic to mammalian cells although the mechanisms are not completely understood. Application of ozone in the process of creating demineralized bone matrix has the potential for several improvements over currently available bone products, including bioburden reduction, sterilization, whitening of the bone, delipidification, and making growth factors within the matrix more available.

To date, those skilled in the art have been unsuccessful in their attempts to overcome the above-identified disadvantages associated with known and available prior art bone substitute compounds. In particular, those skilled in the art have been unsuccessful in identifying and producing bone grafting materials that mimic certain normal bone characteristics by having improved malleable or mechanical properties. In this regard, there is a need in the art for a bone replacement and/or growth enhancement product that (1) precisely mimics normal bone architecture in order to serve as a conduit for vascular and cell immigration; (2) is malleable and elastic; and (3) resists compression, tension, torsion, and bending forces, without fracturing and when deformed has the ability to regain its original shape, structure and size. Therefore, as readily appreciated by those skilled in the art, novel demineralized bone matrices, compositions, and methods for promoting the repair of bone defects that address the disadvantages of the known prior art would be a significant advancement in the art. These matrices have clinical application not only for bone void healing and bone regeneration, but also for cartilage regeneration by providing scaffolding and growth factors to stimulate growth of new tissue in a cartilage defect.

In the presence of saline or body fluids, a bone graft compound that can be compressed to fill a void (in bone or cartilage), which does not dissolve or decompose, and which retains its macro-structure for days or weeks would be a significant advancement in the art. Moreover, demineralized cancellous bone matrices that are osteoinductive, osteoconductive, bioresorbable, biocompatible, substantially similar in structure to bone or cartilage, easy to use and which reduce patient morbidity, and are cost-effective to manufacture would also be a significant advancement in the field.

In addition, there is also a need in the art for demineralized bone matrices that can be used in association with progenitor cells that can be injected and infiltrated into its porous structure to allow attachment, differentiation, proliferation and ultimately function to regenerate new tissue when transplanted or to serve as a 3-D cell culture environment for research and drug screening.

Finally, demineralized bone matrix can also be utilized as a carrier for bioactive agents, attached to the matrix surface by way of a coating, injection or impregnation, designed to release active biologic growth factors or pharmacologic agents immediately or over time. This would be a further advancement over the known prior art.

SUMMARY

The present invention is a method for producing an osteoinductive and osteoconductive demineralized bone matrix. Due to the structural variability of cancellous bone found at different sites within the body and between donors (i.e. variation in porosity and density), no previously described process can consistently produce desired physical properties while limiting the amount of acid exposure, thus minimizing damage to growth factors during demineralization. This invention describes a process in which a bone body is placed in a first processing solution comprising an acid to demineralize the bone body. The bone body is periodically removed from the first solution at specific time intervals to perform at least one test, such as a compression test, on a mechanical property of the bone body. When the test yields a desired result, the bone body is exposed to a second processing solution that is less acidic than the first, thus minimizing the exposure of the bone block to the harsh acidic conditions of the demineralization phase of the process.

BRIEF DESCRIPTION OF THE DRAWINGS

FIGS. 1a and 1b are photographs illustrating an exemplary embodiment of a demineralized cancellous bone matrix produced by the present invention. FIG. 1b shows the demineralized bone matrix in a compressed state, FIG. 1a shows the demineralized bone matrix in a non-compressed state. It can be seen that the compressible nature of the resulting graft allows the demineralized bone matrix to be inserted into a bone defect void in a compressed state with the graft expanding to optimally fill the contours of the bone defect void when the compression force is removed.

FIGS. 3a-3c illustrate the effect of acid exposure on the levels of native growth factors in demineralized cancellous bone. FIG. 3a illustrates the effect of acid exposure on BMP-2. FIG. 3b illustrates the effect of acid exposure on BMP-4. FIG. 3c illustrates the effect of acid exposure on BMP-7. Sample A represents the growth factor content of demineralized cancellous bone matrix processed according to a preferred embodiment of the present invention, showing higher levels of BMPs versus samples B and C. Sample B represents the growth factor content of demineralized cancellous bone matrix processed according to methods currently being practiced in the industry, showing reduced levels of BMPs in comparison with sample A representing the current invention. Sample C represents the growth factor content in demineralized cancellous bone matrix processed by exposure to acid for 24 hours, demonstrating damage or removal of BMPs.

FIGS. 4a-4c illustrate the increase in detectable growth factors in demineralized cancellous bone matrix after exposure of the demineralized cancellous bone matrix to ozonated solution for 20 minutes or 3 hours, as compared to an unozonated (control). FIG. 4a illustrates the increase of BMP-2. FIG. 4b illustrates the increase of BMP-4. FIG. 4c illustrates the increase of BMP-7. The results demonstrate that ozone exposure resulted in greater levels of extracted BMPs obtained from the matrix as measured by ELISA.

FIGS. 5a-5c illustrate the decrease in detectable growth factors in demineralized cancellous bone matrix after exposure of the demineralized cancellous bone matrix to a solution of hydrogen peroxide and water for 15 minutes or 1 hour, as compared to the control. FIG. 5a illustrates the decrease of BMP-2. FIG. 5b illustrates the decrease of BMP-4. FIG. 5c illustrates the decrease of BMP-7. The results demonstrate that hydrogen peroxide exposure resulted in lower levels of extracted BMPs obtained from the matrix as measured by ELISA.

DETAILED DESCRIPTION

Figure 2:
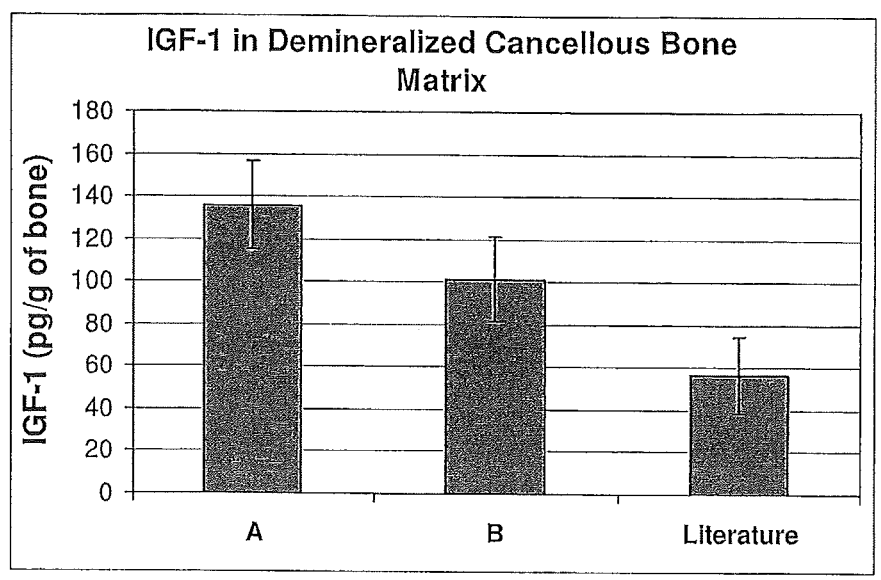
FIG. 2 is a chart, which represents levels of insulin-like growth factor-1 (IGF-1) in three samples of demineralized cancellous bone matrix from the same donor after subjecting the three samples to different demineralization protocols. Samples A and B represent demineralized cancellous bone matrix produced according to the processes, methodologies, and techniques of the present invention. Sample C represents demineralized cancellous bone matrix produced according to the state of the prior art found in the literature, demonstrating damage or removal of IGF-1.

Unless otherwise defined, the technical, scientific, and medical terminology used herein has the same meaning as understood by those skilled in the art. However, for the purposes of establishing support for various terms that are used in the present application, the following technical comments, definitions, and review are provided for reference.

The term "osteoconductive" as used herein refers to a material that facilitates the spontaneous formation of bone by furnishing a microenvironment that supports the ingrowth of blood vessels, perivascular tissue and osteoprogenitor cells into the site where it is deposited The term "osteoinductive" refers to substances within the bone matrix that actively trigger the formation of bone. Osteoinductive material promotes the recruitment of osteoprogenitor cells from an ectopic or an orthotopic site and stimulates their proliferation and differentiation into bone-forming cells, i.e. osteoblasts.

The term "osteogenic" as used herein refers to a substance containing live osteoprogenitor cells in its matrix that actively promote new bone formation.

The term "matrix" as used herein refers to an extracellular matrix of cancellous bone remaining after demineralization. The highly porous cancellous bone matrix provides scaffolding conducive for cell attachment and tissue regeneration.

The term "BMP(s)" as used herein refers to bone morphogeneic proteins that have been associated with bone and cartilage growth through the mechanism of providing signals to osteogenic cells to differentiate, proliferate and regenerate new tissue.

The term "growth factors" as used herein refers to known proteins and hormones that promote neovascularization and growth of new tissue.

In an exemplary embodiment, a demineralized cancellous bone matrix that promotes bone healing, arthrodesis, new bone formation, and repair of pathologic non-union.

Preferably, the demineralized cancellous bone matrix is comprised of one or more large-sized constructs (e.g., 2 mm to several centimeters) of intact demineralized cancellous bone with a residual mineral content less than two percent (<2%).

The novel demineralized cancellous bone matrices of the present invention provide unique and valuable mechanical properties while minimizing damage to (or removal of) native growth factors during demineralization. In an exemplary embodiment, cancellous bone pieces are processed in an acid solution until the bone pieces are compressible to 5 to 60 percent of their original shape while minimizing deterioration to, inactivation of, or elimination of growth factors, intrinsically present in cancellous bone, by removing each cancellous bone piece from a demineralizing acid solution, at specific time intervals, in order to measure compression properties. When each piece is compressible to said percent range, it is prevented from further exposure to the acidic solution by placing it in (or rinsing with) a solution having a pH greater than 4.

In another exemplary embodiment, cancellous bone pieces are processed in an acid solution until they contain less than 2 percent residual calcium, or magnesium, or phosphate by weight and the bone pieces are compressible to 5 to 60 percent of their original shape, while minimizing deterioration to, inactivation of, or elimination of growth factors, intrinsically present in cancellous bone.

In an additional exemplary embodiment, cancellous bone pieces are processed in an acid solution until the bone pieces are compressible to less than 60 percent of their original shape, using between 10 and 1000 grams-force/cm$^2$, while minimizing deterioration to, inactivation of, or elimination of growth factors, intrinsically present in cancellous bone. Each cancellous bone piece is removed from a demineralizing acid solution, at specific time intervals, in order to measure compression properties, such that when each piece is compressible to said percent range it is prevented from further exposure to the acidic solution by placing it in (or rinsing with) a solution with a pH greater than 4.

In another exemplary embodiment, cancellous bone pieces are processed in an acid solution in order to demineralize the bone bodies. Periodically the bone is removed in order to measure the compression force versus the percentage of size reduction when the bone body is under the compression force. The result of the compression force versus the compressed size determines the next step in the bone processing. The outcome of the testing determines both the acid concentration the bone body will next be soaked in and the time period for which it will be soaked before the compression force and compressed size are measured again. This step is repeated until the bone body is compressible to 5 to 60 percent, of its original shape, using between 10 and 1000 grams-force/cm$^2$. This process minimizes deterioration to, inactivation of, or elimination of growth factors, intrinsically present in cancellous bone, by removing each cancellous bone piece from a demineralizing acid solution, at specific time intervals, in order to measure compression properties. When each piece is compressible to the aforementioned percent range, it is prevented from further exposure to the acidic solution by placing it in (or rinsing/spraying/dipping/soaking with) a solution having a pH greater than 4.

Furthermore, the physical and chemical characteristics and structure of the demineralized bone matrices of the present invention allow for coating or impregnating bioactive agents, including growth factors, that are designed to elute into the surrounding tissues. In an exemplary embodiment, the surface of the demineralized bone matrix may be in immediate contact with the surrounding host tissues and fluids. Since the demineralized bone matrix maintain normal bone shape and structure, it will not dissolve and ooze from a bone defect, void, or mechanical device to which it may be applied for insertion into said bone defect or void. Since the demineralized bone matrix has an open porous structure, active proteins present on the surface of the matrix are not hidden from the host environment by a carrier that are typically present in putties and gels. There is no dilution of the bone by carriers, therefore the demineralized bone matrix graft will have a higher content of bone compared with currently available putties and gels that are often less than 30% total bone content.

An exemplary embodiment of the present invention may be directed to a method of cutting, shaping, or molding the demineralized cancellous bone matrix to fit specific shapes and contours needed to conform to associated mechanical devices like spinal cages, acetabular cups, tubes, and cylinders. In addition, the present invention is directed to demineralized cancellous bone matrices that can be used alone as a scaffold or bone void filler, or in conjunction with other metallic, plastic, or composite devices, relying on its biologic and mechanical characteristics to promote bone healing, fill a space, to maintain its essential structure, and bridge separate bony surfaces without fracturing or failing under compressive, tensile, bending, or torsional loads.

As noted above, the demineralized cancellous bone matrices of the present invention may be configured to fit inside a mechanical device like a spinal cage. If engageably introduced into a mechanical device like a spinal cage dry, the demineralized cancellous bone matrix will expand in the device when hydrated to completely fill the device with tight apposition against host bone on either side of the mechanical device. Accordingly, the demineralized cancellous bone matrix may be compressed to fit into the irregularities that can often result from bone loss due to cystic change, degeneration of bone, osteoporosis, or prosthetic revision between bone and an artificial joint implant like an acetabular cup, femoral stem, or other arthroplasties. When compressed, the demineralized cancellous bone matrix will tend to reversibly deform to fit the surrounding contours, but with its elasticity, it will expand to fill adjacent voids without oozing out of the bony defect or void.

Special physical properties of the demineralized bone matrix may include, for example: (1) volume change with hydration, elasticity to compression, tension, torsion, bending, and compressibility, etc.; (2) different physical characteristics depending on whether the demineralized bone matrix are hydrated or non-hydrated; (3) capable of mixing with blood, bone marrow aspirate, blood products, and the like; (4) expanding with hydration to fill a void without losing its tensile properties; (5) will not dissolve with irrigation or time like other prior materials such as putties, devices and methods; (6) will not lose its tensile properties when infiltrated by body fluids; (7) capable of conforming to irregular shapes without fracturing or losing basic biologic attributes; (8) capable of absorbing blood and fluid and expand with hydration; and (9) capable of tolerating cyclic loading in tension, compression, bending and torsion without early fatigue fracture.

The present invention demonstrates improved biological properties in promoting bone repair and growth. Optimized processing of the demineralized bone matrix will allow for retention of native growth factors and yields a matrix that has higher growth factor levels and enhanced osteoinductive properties. The demineralized bone matrices, in accordance with the present invention, may be osteoinductive, osteoconductive, osteogenic, and combinations thereof. The highly porous nature of the demineralized cancellous bone matrix results in a natural scaffold for cell attachment and other cellular activities that lead to tissue regeneration. Cells from the patient, including osteoprogenitor cells, readily attach to the demineralized cancellous bone matrix and grow new tissue. Moreover, the demineralized bone matrices may have universal application in many bone graft procedures, for example and not by limitation, orthopedic surgery, neurological surgery, plastic surgery, dental surgery, dermatologic surgery, and the like.

A further improvement in the design and function of the present invention is the use of ozone in the processing protocol for several purposes, including enhanced availability of growth factors including BMPs that are associated with the collagen matrix following demineralization, enhanced delipidification and whitening of the matrix during processing, and decontamination and sterilization of the matrix.

In addition, demineralized cancellous bone matrices of the present invention may have application to many disease states, for example and not by limitation, spine fractures and disc degeneration, osteoporosis or osteopenia, orthopedic fracture and joint degeneration, cartilage repair, dental procedures, and the like.

An exemplary embodiment of the present invention includes the use of the demineralized cancellous bone matrices prepared in accordance with the processes, methodologies, and techniques of the present invention may be used as material for the 3-D culturing of cells, including osteogenic progenitor cells, pre-osteoblasts, bone forming cells, cartilage forming cells, stem cells, and other progenitor cell types. These cells may be autogenic, allogeneic, or xenogenic. The cells may be delivered to the matrix via carriers made from gelatin, fibrin, cellulose, synthetic extracellular matrices, polymers, and other biocompatible carriers. The cells may be injected into the hydrated matrix and then placed in culture media. These cell seeded constructs may be used for implantation into patients for regeneration of tissue, or as 3-D cell culture models for research or drug screening purposes.

The demineralized bone matrices of the present invention have substantial applicability and utility over prior art methods and materials by means of improved conformability relative to its sponge-like matrix while minimizing damage to (or removal of) native growth factors during demineralization An additional embodiment is for implantation into bone or cartilage defect sites with unique shapes, and sizes for improved bone graft success or cartilage repair success. Additionally, improved conformability of the sponge-like demineralized bone graft matrix is easily incorporated into various cages and other devices for bone graft procedures.

The American Academy of Orthopedic Surgeons and the American Association of Tissue Banks have suggested a list of attributes for an ideal bone graft substitute (BGS), but these groups have also stated that the ideal has yet to be achieved. These cited properties include, for example and not by limitation: (1) biocompatible; (2) bioresorbable; (3) osteogenic (i.e., capacity of the cellular elements of the transplanted graft to survive and directly form new bone); (4) osteoconductive; (5) osteoinductive; (6) structurally similar to bone; (7) easy to use; (8) malleable; and (9) deformable. The demineralized cancellous bone matrix of the present invention meets all of these criteria by itself, except for having osteogenic properties. However, if the demineralized cancellous bone matrix is infiltrated with bone marrow aspirate or if coated or infiltrated with stem cells, the demineralized cancellous bone matrices would meet all of the criteria listed for an ideal implant by the Academy of Orthopedic Surgeons and by the American Association of Tissue Banks.

The following examples will illustrate the practice of the present invention in further detail. It will be readily understood by those skilled in the art that the following methods, formulations, and compositions of novel compounds of the present invention, as generally described and illustrated in the examples herein, are to be viewed as exemplary of the principles of the present invention, and not as restrictive to a particular structure or process for implementing those principles. Thus, Examples 1-6, are not intended to limit the scope of the invention, as claimed, but are merely representative of exemplary embodiments of the invention.

EXAMPLES

Example 1

A method for preparing demineralized cancellous bone pieces as described in the present invention may include the steps of: (1) adding from 1-300 grams of cancellous bone matrix to 10-4500 mL of 0.3-2.0 M hydrochloric acid (HCl) in a suitable reaction vessel; (2) stirring the vessel contents for approximately 4-10 hours; (3) replacing "spent" acid solution in the beaker every 1-4 hours; (4) removing each piece of cancellous bone matrix every 5-90 minutes and performing tests to determine whether the block is fully compressible; and (5) transferring pieces of cancellous bone matrix that are fully compressible to a neutralizing solution having a pH of >4 and returning the pieces of cancellous bone matrix that are not fully compressible to the acid containing reaction vessel to continue for further demineralization and repeated compression testing as described above.

Example 2

Use of Ozone to Improve Function of Demineralized Cancellous Bone Matrix

A method for improved function of demineralized cancellous bone matrix by treating said bone with ozone during the processing of the tissue may include the steps of: (1) placing demineralized cancellous bone matrix in an ozone enriched solution containing microbubbles; (2) with continual replacement of the solution containing an ozone concentration of 0.1 to 400 ppm; (3) with an exposure time of 0.1 to 7 hours; at a temperature range of the ozone solution of −20 to 50 C. Ozone solution treatment of the bone could also take place prior to demineralization using the same parameters discussed above.

Example 3

Clinical Applications for Demineralized Cancellous Bone Matrix

The following are examples of clinical applications and uses for the novel demineralized cancellous bone matrix:

Use in Spinal Implants: This example demonstrates some of the biologic and mechanical properties of demineralized cancellous bone matrices and demineralized cancellous bone matrix compounds prepared in accordance with the present invention when used in association with a mechanical device to create a fusion and facilitate healing between surfaces of adjacent vertebral bodies.

The novel demineralized cancellous bone matrices of the present invention may be placed in a space or void provided by an anterior spinal implant (e.g., spinal cage or other device comprised of metal, bone, plastic, or other composite material). The demineralized bone graft matrix compresses allowing it to be fit into various shaped spaces without fracturing the demineralized cancellous bone matrix and then expands to fill the void within the device. As the demineralized cancellous bone matrix is hydrated, without oozing from the device and without dissolving in the presence of saline, irrigant, or body fluids, the demineralized cancellous bone matrix expands to tightly abut the adjacent bone surfaces creating an osteogenic, osteoinductive, and osteoconductive bridge that may be used alone or in conjunction with other bone putties or gels, active biologic or pharmacologic coatings, blood or bone marrow aspirate.

Alternatively, a demineralized cancellous bone matrix compound, comprised of various pieces of demineralized cancellous bone matrix with other constituents (for example, with or without bone marrow aspirate or platelet gel), can be placed in a space or void provided by an anterior spinal implant (spinal cage or other device comprised of metal, bone, plastic, or other composite material). The demineralized cancellous bone matrix compound compresses to allow it to be fit into various shaped spaces without fracturing and then expands to fill the void within the device without oozing from the device, without dissolving in the presence of saline, irrigant, or body fluids, the demineralized cancellous bone matrix compound expands to tightly abut the adjacent bone surfaces creating an osteogenic, osteoinductive, and osteoconductive bridge that may be used alone or in conjunction with other bone putties or gels, active biologic or pharmacologic coatings, blood or bone marrow aspirate.

Use in Structural Spinal Cortical/Cancellous Allograft This example demonstrates that a demineralized cancellous bone matrix or demineralized cancellous bone matrix compound prepared in accordance with the present invention may be used in conjunction with structural spinal cortical or cortical/cancellous allograft. A dowel or precision milled spinal allograft cut from the tibia, femur, humerus, fibula, tarsal or other bone provides structural support between two adjacent vertebral bodies like a spinal implant. When the dowel is hollow, the demineralized cancellous bone matrix may be placed in the center of the dowel to create a fusion and facilitate healing between surfaces of the adjacent vertebral bodies. The demineralized cancellous bone matrix may be cut into a ring configuration or other variable shape and design to fit around the outside of cortical allograft to create a fusion and facilitate bone healing.

Use in Delayed Union or Non-Unions of Bone: This example demonstrates an exemplary embodiment of using the unique mechanical and biologic properties of demineralized cancellous bone matrices prepared in accordance with the processes, methodologies, and techniques of the present invention to create a healing bridge across delayed unions of bone or non-unions of bone by placing a demineralized cancellous bone matrix across the pathologic space.

A canal may be drilled from one healthy bone end across the non-healing space and into the second healthy bone. Using a novel device consisting of a size rasp, an inserter with a plunger, a demineralized cancellous bone matrix formed as a cylinder or dowel with or without active biologic or pharmacologic coatings, may be placed into the canal, thus bridging one healthy bone with another. The novel characteristics of the demineralized cancellous bone matrix allows it to be compressed into the inserter and when hydrated in the canal with saline, blood, bone marrow aspirate, or other fluid substance, the demineralized cancellous bone matrix expands to tightly fill the space. Because the demineralized cancellous bone matrix is elastic and will deform to compressive, tensile, torsional, and bending forces, some movement at the non-union site will not cause the bridging graft to fatigue and fracture. As contemplated herein, the demineralized cancellous bone matrix of the present invention, because of its structural features, may be used with all manner of orthopedic fixation such as plates and screws: intramedullary fixation, pins or wires, external fixation devices, a cast, splint, or brace.

Use in Distraction Osteogenesis: This example demonstrates an exemplary embodiment of using the present invention to promote and hasten bone healing in distraction-osteogenesis (bone lengthening or transport). A demineralized cancellous bone matrix bridge may be placed at the corticotomy or osteotomy site, either at the time of surgical creation of the bone defect or some time later. The demineralized cancellous bone matrix may be placed within the canal or within a distraction callous either with or without use of the insertion device or a variant of the device.

A demineralized cancellous bone matrix bridge may be used in distraction-osteogenesis with all manner of orthopedic fixation such as plates and screws, intramedullary fixation, pins or wires, external fixation devices, a cast, splint, or brace.

Use in Fracture Healing: This example demonstrates an exemplary embodiment of using the present invention to promote fracture healing at acute fracture sites.

A canal may be drilled from one bone end across the fracture space and into the second bone. A bone graft application kit, in accordance with the present invention, may include a size rasp, an inserter with a plunger, a demineralized cancellous bone matrix cylinder or dowel with or without active biologic or pharmacologic coatings, which may be placed into the canal, thus bridging one healthy bone with another. The novel characteristics of the demineralized cancellous bone matrix allows it to be compressed into the inserter and when hydrated in the canal with saline, blood, bone marrow aspirate, or other fluid substance, the demineralized cancellous bone matrix will expand to tightly fill the space. Because the demineralized cancellous bone matrix is elastic and will deform to compressive, tensile, torsional, and bending forces, some movement at the nonunion site will not cause the bridging graft to fatigue and fracture.

The demineralized cancellous bone matrix may be placed into the medullary space at the fracture site at the time of surgical repair either with the inserter or manually. It can be placed in the form of a cylinder or dowel or as fragment pieces, as desired. The demineralized cancellous bone matrix bridge in accordance with the present invention may be used with all manner of orthopedic fixation such as plates and screws, intramedullary fixation, pins or wires, external fixation devices, a cast, splint, or brace.

Use in Arthrodesis Healing: This example demonstrates an exemplary embodiment of using the present invention to enhance and promote successful healing at an arthrodesis site where the joint between two bones is removed and an attempt is made to obtain bone fusion or arthrodesis between the remaining bones; joints typically fused or arthrodesis are the bones of the fingers, toes, wrist, foot and ankle. The ankle joint is at especially high risk for failure of fusion. Other joints commonly fused include the shoulder, elbow, hip, and knee joints. The demineralized cancellous bone matrix of the present invention can be used with anterior and posterior spinal segments, including facet joints, any moveable or nonmovable joint, including sacro-iliac joints, pubis, and acromio-clavicular joint, and sterno-clavicular joints.

A canal may be drilled from one healthy bone end across the arthrodesis site and into the second healthy bone. Using a novel device consisting of a size rasp, an inserter with a plunger, a demineralized cancellous bone matrix formed as a cylinder or dowel with or without active biologic or pharmacologic coatings, the demineralized cancellous bone matrix may be placed into the canal, thus bridging one healthy bone with another. The novel characteristics of the demineralized cancellous bone matrix allow it to be compressed into the inserter and when hydrated in the canal with saline, blood, bone marrow aspirate, or other fluid substance, the demineralized cancellous bone matrix will expand to tightly fill the space. Because the demineralized cancellous bone matrix is elastic and will deform to compressive, tensile, torsional, and bending forces, some movement at the non-union site will not cause the bridging graft to fatigue and fracture. The drill used may or may not be the same diameter as drills used with standard internal fixation devices, and may or may not be used with cannulated drills.

Use in Improving Fixation in Arthroplasties: A novel device in accordance with the present invention may be used to fill defects in bone and hasten and/or facilitate healing of bone. Demineralized cancellous bone matrices prepared in accordance with the processes, methodologies, and techniques of the present invention may be placed within a defect in bone resulting from trauma, cyst, tumor, previous surgery, or infection. The demineralized cancellous bone matrix may be packed in the defect as a single block or in multiple fragments that might range in size from 2 mm to several centimeters. The demineralized cancellous bone matrix and smaller fragments of bone matrix (e.g., compound) may be used in association with joint arthroplasties to improve fixation and fill defects such as those adjacent to acetabular cups in the pelvis, around femoral stems, adjacent to knee components of the distal femur, proximal tibia and adjacent to components reconstructing the joints of the hand, wrist, elbow, shoulder, foot, ankle, or other articulating surfaces.

The unique structural and functional features of the demineralized cancellous bone matrices of the present invention allow for compression to facilitate placement into various shaped spaces or cavities without fracturing. The demineralized cancellous bone matrix expands to fill the void within the device as it is hydrated without oozing from the device, without dissolving in the presence of saline, irrigant, or body fluids; the demineralized cancellous bone matrix expands to tightly about the adjacent bone surfaces creating an osteogenic, osteoinductive, and osteoconductive bridge that may be used alone or in conjunction with other bone putties or gels, active biologic or pharmacologic coatings, blood or bone marrow aspirate.

Use in Cartilage Repair and Regeneration: This example demonstrates an exemplary embodiment of using the present invention for cartilage repair by placement of the matrix in a lesion in the cartilage to encourage cartilage regeneration. The present invention allows for compression to facilitate placement into various cartilage defects or cavities within and in association with cartilage. The hydrated demineralized cancellous bone matrix expands to fill the void within the cartilage and may absorb blood or bone marrow. The demineralized cancellous bone matrix may be coated or injected with growth factors or stem cells to further enhance repair and regeneration of cartilage.

Use in Oral Surgery: This example demonstrates an exemplary embodiment of using the present invention for reconstructing mandible and maxilla bone in reconstructive oral surgery. A demineralized cancellous bone matrix of the present invention may be placed into cavities or spaces in the jaw and maxilla as graft to recreate lost bone. The demineralized cancellous bone matrix may be used with or without demineralized cortical bone powder, with or without carriers or other active biologic or pharmacologic agents. At least two presently preferred uses of the present invention are contemplated for use in oral surgery and are present in this example. A pre-selected and/or appropriate sized demineralized bone graft material in accordance with the present invention may be inserted in a tooth extraction socket. If appropriate, an osseous alveolar defect may also be repaired in the same fashion using bone graft materials in accordance with the present invention. A membrane of choice may be placed over the demineralized bone graft material in accordance with the present invention and may be sutured at the gingival level.

An appropriately sized and hydrated demineralized cancellous bone matrix processed in accordance with the processes, methodologies, and techniques of the present invention may be inserted through the sinus window and may be placed into a surgically created sinus cavity. This exemplary embodiment of the present invention may have one or more of the following advantages over known prior art. First, ease of application—the demineralized cancellous bone matrices or compounds comprising same of the present invention may be more easily inserted into the graft site relative to prior art graft materials and methods. As noted herein, the demineralized cancellous bone matrix may be formulated as a single piece of compressible material compared to traditional (i.e., prior art) grafting materials that may be particulate or putty like in consistency and thus may be more difficult to place at a graft site. Second, the demineralized cancellous bone matrix of the present invention may be compressed prior to placement at a desired graft site and may then expand after placement. In contrast, prior art bone graft materials need to be packed into a graft site. Third, the bone graft matrix or derived compounds may not migrate, eliminating the need to use membranes for coverage. Finally, the demineralized cancellous bone matrices of the present invention may result in faster bone formation allowing faster placement of dental implants.

Use in Healing Infected Bone: This example demonstrates an exemplary embodiment of using the present invention for enhancing or promoting healing in the presence of infected or contaminated bone and soft tissues when attempting to heal an infected non-union of bone; when attempting to fuse an infected joint either primarily or after a failed total joint arthroplasty; when attempting to internally or externally fix an acute or old fracture; when attempting to fuse an infected spinal segment either primarily or after a previously failed spinal fusion; when attempting to lengthen and transport bone in a previously infected bone segment. Demineralized bone graft materials treated with a elutive coating designed to release antibiotic or anti-infective agents such as: silver sulfadiazine, chlorhexidine, gentamicin, tobramycin, vancomycin or others. Demineralized bone graft materials soaked in an antibiotic or anti-infective solution containing active agents such as: silver sulfadiazine, chlorhexidine, gentamicin, tobramycin, vancomycin or others. The demineralized bone graft material may be packed into the affected area as a block, as smaller fragments or introduced as a cylinder.

Vertebroplasty Application: Osteoporosis thins the bones of some 10 million Americans. Some 700,000 patients a year suffer spinal fractures as a result. They're excruciating since sitting or standing compresses the broken vertebra. About two-thirds of patients become pain-free after a few months of bed rest, but the rest have chronic pain. And spinal fractures accumulate, stealing height and causing digestion and breathing problems. Using a vertebroplasty approach that is currently available, the sponge-like bone material incorporated into the biodegradable glue would be injected into the crushed vertebra, where it will expand and provide immediate pain relief and supporting structure for the vertebra, and agents which will stimulate bone regrowth. Current vertebroplasty techniques use a cement (e.g., methylmethacrylate glue) to stabilize the bone and to prevent or delay further collapse. There is evidence that patients receive relief with this technique, with small studies suggesting anywhere from 75 to 90 percent of patients get pain relief.

A newer technique called Kyphoplasty is more complicated. First a catheter bearing a balloon may be threaded into the cracked vertebra. Inflating the balloon with a special liquid jacks up the collapsed bone so the cement can then be injected, restoring some height. The advantage of the invention is that the cement used in the currently available procedures does not encourage bone growth. The pain relief is usually only temporary, and within a few months the patients are again having problems. Our use of bone compatible materials, and materials that encourage bone growth will facilitate the potential for a more permanent recovery of structure and function of osteoporotic bone. The expandable nature of the sponge-like bone material combined with biodegradeable glue could be exploited to provide immediate height restoration and vertebral stability for the patient.

Example 4

Delivery of Bioactives to Wound Site

A method delivery of bioactives using the demineralized cancellous bone matrix as a carrier via; (1) bioactive impregnation of the matrix by placing the dehydrated or hydrated demineralized cancellous bone matrix in a solution containing the bioactive, whereby the matrix 'soaks' up the solution, followed by air or freeze drying; (2) or by coating the demineralized cancellous bone matrix with a hydrogel, polymer or other material that contains a bioactive; (3) or by injecting a solution containing a bioactive into the matrix.

These and other active proteins could be infiltrated, impregnated or injected into the demineralized cancellous bone matrix or coated onto the demineralized surface. The proteins could be placed adjacent to the demineralized cancellous bone matrix by way of another carrier and thus imparted to the immediate surgical bed. The demineralized cancellous bone matrices make an ideal carrier for these proteins because of its described mechanical properties, it elasticity, its flexibility, its osteoinductive properties, its osteoconductive properties, its absorbency and ability to hold onto fluids when hydrated.

The demineralized cancellous bone matrix compound prepared in accordance with the processes, methodologies, and techniques of the present invention can be combined with these and other active proteins and could be mixed into the demineralized cancellous bone matrix compound or coated onto the demineralized particle surface or surface of another substance used with the bone compound. The proteins could be placed adjacent to the demineralized cancellous bone matrix by way of another carrier and thus imparted to the immediate surgical bed. The demineralized cancellous bone matrix makes an ideal carrier for these proteins because of its described mechanical properties, it elasticity, its flexibility, its osteoinductive properties, its osteoconductive properties, its absorbency and ability to hold onto fluids when hydrated.

Example 5

Creation of 'Inert' Bone Matrix

Demineralized bone matrix may be processed in such a way as to purposefully reduce the availability of growth factors within the matrix by utilizing known adverse treatments. This will provide an 'inert' matrix, consisting of mostly extracellular components, primarily collagen, without significant signal molecule content. Such a matrix may be desirable in some clinical and research settings. Further processing demineralized bone by hydrogen peroxide exposure is one method to accomplish this goal.

Example 6

Use of Demineralized Cancellous Bone Matrix as a 3-D Scaffold

A method for the use of the demineralized cancellous bone matrices prepared in accordance with the processes, methodologies, and techniques of the present invention as material for the three dimensional (3-D) culturing of cells, (1) the cells are delivered to the matrix via carriers made from gelatin, fibrin, cellulose, synthetic extracellular matrices, polymers, and other biocompatible carriers (2) or the cells are placed in culture directly onto the matrix; (3) or the cells are injected into the hydrated matrix and then placed in culture media; (4) complete nutritive medias is used in cultures containing the demineralized cancellous bone matrix with cells; (5) additional media components of additives such as cell differentiation factors; (6) the 3-D matrix in vitro cell culture continues until mature tissue formation occurs, and then is implanted; (7) or conversely, may be transplanted shortly after the cells are associated with the matrix, with tissue regeneration occurring in vivo; (8) the demineralized cancellous bone matrix cell culture constructs will be used to perform drug or chemical screening to assess trophic or toxic agents by exposing cell seeded constructs in vitro to chemicals of interest and assessing cell viability or function; (9) kits will consist of samples of prepared demineralized cancellous bone matrix, with and without reagents or cells appropriate for the specific field of interest.

These cultures of cells in the demineralized cancellous bone matrix may be used to grow bone or cartilage for transplantation to repair bone or cartilage defects or other tissue or organ defects in humans or animals. Cell seeded scaffolds may be cultured in vitro until mature tissue formation occurs, and then implanted, or conversely, may be transplanted shortly after the cells are associated with the matrix, with tissue regeneration occurring in vivo. For example, chondrocytes may be grown in vitro on the demineralized cancellous bone matrix, to form cartilage tissue that may then be implanted into an area of injured cartilage to repair and regenerate the tissue.

The demineralized cancellous bone matrix cell culture constructs may also be used as a research model to perform drug or chemical screening to assess trophic growth enhancing or stem cell differentiation agents or possible toxic agents in a 3-D culture setting. Current testing is often performed using 2-D culturing of cells and it is known to those familiar in the art that results from 2-D cultured cells are often different from those cells cultured in 3-D matrices, which is a more natural environment to cells of all types. Kits may provide samples of prepared demineralized cancellous bone matrix, with and without reagents or cells appropriate for the specific field of interest.

Demineralized cancellous bone matrix readily absorbs, within the collagen fibers, many kinds of bioactives, as well as stains and dyes and therefore extends said bone matrices uses to cellular attachment/adhesion and growth research where the bioactives, stains, and dyes elute from the matrix surface. Demineralized cancellous bone matrix can be sliced into thin sheets for improved observation of cellular activities and remodeling of the extracellular matrix. Xenogenic materials are readily available, and hence particularly attractive for research applications.

Cancer cells can also be grown on this matrix to assess chemotherapeutic agents. Autologous cancer cells may be used, and chemotherapeutic agents could be screened to tailor the specific anti-cancer drug combination most effective for tumor suppression or elimination in a given patient.

As will be appreciated, the present invention may be embodied in other specific forms without departing from its spirit or essential characteristics. The described embodiments are to be considered in all respects only as illustrative, and not restrictive.

Although the present invention has been described with reference to preferred embodiments, workers skilled in the art will recognize that changes may be made in form and detail without departing from the spirit and scope of the invention.

The invention claimed is:

1. A method for producing a three dimensional matrix, comprising:
    seeding a demineralized bone matrix with cells to form the three dimensional matrix, wherein the demineralized bone matrix was produced by a method comprising:
    placing a bone body in a first processing solution comprising an acid to demineralize the bone body, wherein the demineralized bone body comprises bone fragments with at least one dimension greater than 2 mm;
    periodically removing the bone body from the first processing solution to perform at least one test on a mechanical property of the bone body; and
    exposing the bone body to a second processing solution when the test yields a desired result to produce a demineralized bone matrix, wherein the demineralized bone matrix comprises less than 2% residual calcium, wherein the test comprises a compression test on the bone body, wherein the compression test comprises applying a compressive force in a range from about 10 g-force/cm$^2$ to about 4000 g-force/cm$^2$ until the bone body uniformly compresses to less than about 60 percent of its original shape; or wherein the test comprises a bending test, wherein the bending test comprises applying a bending force in a range from about 10 g-force/cm$^2$ to about 4000 g-force/cm$^2$.

2. The method of claim 1, further comprising culturing the cells in the three dimensional matrix.

3. The method of claim 2, wherein the step of culturing the cells is conducted to establish cell attachment.

4. The method of claim 1, further comprising contacting the three dimensional matrix with factors for cellular differentiation and proliferation of the cells.

5. The method of claim 4, further comprising studying new tissue growth, cell differentiation, proliferation, and function in the three dimensional matrix.

6. The method of claim 1, wherein the cells are selected from the group consisting of osteoprogenitor cells, skeletal muscle stem cells, cartilage progenitor cells, differentiated osteoblasts, osteoclasts, chondrocytes, adipose stem cells, bone marrow stem cells, mesenchymal stem cells, adult stem cells, embryonic stem cells, and combinations thereof.

7. The method of claim 1, wherein the cells are selected from the group consisting of autogenic cells of a patient, allogeneic cells of the patient, xenogenic cells of the patient, and combinations thereof.

8. The method of claim 1, further comprising mixing the cells with a biocompatible carrier selected from the group consisting of fibrin, gelatin, cellulose, synthetic extracellular matrices, synthetic polymers, natural polymers, and combinations thereof to form a cell-containing carrier.

9. The method of claim 8, wherein the step of seeding comprises injecting the three dimensional matrix with the cell-containing carrier.

10. The method of claim 1, wherein the demineralized bone matrix is a sponge-like bone graft matrix.

11. The method of claim 1, further comprising coating the three dimensional matrix with bone marrow aspirate or stem cells.

12. The method of claim 1, wherein the demineralized bone matrix comprises less than 2% of magnesium or phosphate.

13. The method of claim 1, wherein the demineralized bone matrix is compressible to 5 to 60% of an original shape.

14. The method of claim 1, wherein the first processing solution has a pH between about 0 and about 0.5.

15. The method of claim 1, wherein the second processing solution has a pH greater than about 4.

16. The method of claim 1, wherein the test comprises the bending test, and wherein the bending force does not cause the cortical bone body to fracture.

17. The method of claim 1, wherein the matrix is compressible to 5 to 60 percent of an original shape of the matrix when between 10 and 1000 grams-force/cm$^2$ of force is applied to the matrix and wherein the matrix is a sponge-like bone graft matrix.

18. The method of claim 1, further comprising adding an additive to the three dimensional matrix, wherein the additive is selected from the group consisting of a bioactive agent, a chemotherapeutic agent, a chondrocyte, a trophic growth enhancing agent, and combinations thereof.

19. The method of claim 1, wherein the demineralized bone matrix has two or more of the characteristics selected from the group consisting of:
   a. having greater than about 5000 pg/g of demineralized bone of bone morphogenetic protein-2 (BMP-2);
   b. having greater than about 600 pg/g of demineralized bone of bone morphogenetic protein-4 (BMP-4)
   c. having greater than about 12000 pg/g of demineralized bone of bone morphogenetic protein-7 (BMP-7); and
   d. having greater than about 60 pg/g of demineralized bone of insulin-like growth factor-1 (IGF-1) per gram.

20. The method of claim 1, wherein the demineralized bone matrix is not subjected to hydrogen peroxide.

* * * * *